(12) United States Patent
Dwivedi et al.

(10) Patent No.: US 8,962,851 B2
(45) Date of Patent: Feb. 24, 2015

(54) ONE-POT PROCESS FOR THE PREPARATION OF BENZIMIDAZOLE DERIVATIVES

(71) Applicant: Cadila Healthcare Limited, Tal. Padra, Dist. Vadodara, Gujarat (IN)

(72) Inventors: Shriprakash Dhar Dwivedi, Gujarat (IN); Ashok Prasad, Gujarat (IN); Daya Ram Pal, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 13/727,338

(22) Filed: Dec. 26, 2012

(65) Prior Publication Data

US 2013/0296376 A1      Nov. 7, 2013

(30) Foreign Application Priority Data

Dec. 27, 2011  (IN) .............................. 3671/MUM/11

(51) Int. Cl.
  *C07D 401/00* (2006.01)
  *A61K 31/44* (2006.01)
  *C07D 401/12* (2006.01)

(52) U.S. Cl.
  CPC .................................... *C07D 401/12* (2013.01)
  USPC .......................... 546/339; 546/273.7; 514/338

(58) Field of Classification Search
  None
  See application file for complete search history.

(56) References Cited

U.S. PATENT DOCUMENTS 8,394,963 B2 *   3/2013   Rao et al. ................... 546/273.7

* cited by examiner

*Primary Examiner* — Heidi Reese
(74) *Attorney, Agent, or Firm* — Ladas & Parry LLP (57) ABSTRACT

The present invention discloses one pot process for enantioselective synthesis of single enantiomers of substituted sulphoxides 2-(2-pyridinylmethylsulphinyl)-1H-benzimidazoles or said compounds in an enantiomerically enriched form.

28 Claims, 2 Drawing Sheets

ONE-POT PROCESS FOR THE PREPARATION OF BENZIMIDAZOLE DERIVATIVES

FIELD OF THE INVENTION

The invention relates to a one-pot process for the preparation of benzimidazole derivatives and pharmaceutically acceptable salts thereof. In particular, the invention relates to one-pot process for enantioselective synthesis of single enantiomers of substituted sulphoxides 2-(2-pyridinylmethylsulphinyl)-1H-benzimidazoles or said compounds in an enantiomerically enriched form. More particularly, the invention relates to a one-pot process for the preparation of esomeprazole magnesium dihydrate. Also, the invention provides pharmaceutical composition of esomeprazole magnesium prepared by using a one-pot process.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Omeprazole is chemically known as 5-methoxy-2-[[(4-methoxy-3,5-dimethyl-2-pyridinyl)methylsulfonyl]-1H-benzimidazole. The S-enantiomer of omeprazole, "esomeprazole", is chemically known as (S)-5-methoxy-2-2-[[(4-methoxy-3,5-dimethyl-2-pyridinyl)methylsulfonyl]-1H-benzimidazole. Esomeprazole is a proton pump inhibitor used in the treatment of dyspepsia, peptic ulcer disease, gastroesophageal reflux disease and Zollinger-Ellison syndrome. Esomeprazole magnesium salt is marketed as NEXIUM® and is represented by Formula (I).

There are a large number of patents and patent applications disclosing different substituted 2-(2-pyridinylmethylsulphinyl)-1H-benzimidazoles. This class of compounds has properties making the compounds useful as inhibitors of gastric acid secretion and generally known as proton pump inhibitors.

For example, the compound (5-methoxy-2-[[(4-methoxy-3,5-dimethyl-2-pyridyl)methyl]sulfinyl]-1H-benzimidazole), with the generic name omeprazole, described in EP 5129. It is marketed under the brand name Prilosec® for treatment of duodenal ulcer, gastric ulcer and GERD; maintenance of healing of errosive esophagitis, and long term treatment of pathological hyperscretory conditions.

Rabeprazole is another compound of the same class and chemically known by 2-[[[(4-(3-methoxypropoxy)-2-methyl-2-pyridinyl]methyl]sulfinyl-1H-benzimidazoles. It was reported in U.S. Pat. No. 5,045,552 and marketed in the United States under the brand name Aciphex® for healing of erosive or ulcerative GERD, maintenance of healing of GERD and treatment of symptomatic GERD.

Pantoprazole is the active ingredient of a pharmaceutical product that is marketed in the United States by Wyeth-Ayerst Inc. under the brand name Protonix®. Pantoprazole is chemically represented (5-(difluoromethoxy)-2-[[(3,4-dimethoxy-2-pyridinyl)methyl]-sulfinyl]-1H-benzimidazole. Pantoprazole useful for short-term treatment of erosive esophagitis associated with gastroesophageal reflux disease (GERD), maintenance of healing of erosive esophagitis and pathological hypersecretory conditions including Zollinger-Ellison syndrome.

Lansoprazole, another compound represented by 2-[[[3-methyl-4(2,2,2,-trifluoroethoxy)-2-pyridiyl]methyl]sulfinyl]-1H-benzimidazole and reported in U.S. Pat. No. 4,628,098. It is marketed under the brand name Prevacid® for short-term treatment of duodenal ulcer, H. Pylori eradication to prevent recurrence of duodenal ulcer and maintenance of healed duodenal ulcers.

The single enantiomers of pharmacologically active compounds have met an increased interest in the last years because of improved pharmacokinetic and biological properties. Therefore, there is a demand and need for an enantioselective process that can be used in large scale for the manufacture of the single enantiomers of pharmacologically active compounds, such as for instance optically pure, substituted 2-(2-pyridinylmethylsulphinyl)-1H-benzimidazoles.

There are several patents and patent applications disclosing oxidation of prochiral sulfide. U.S. Pat. No. 5,948,789 describes oxidation of a pro-chiral sulfide with an oxidizing agent and chiral titanium complex in an organic solvent. U.S. Pat. No. 6,166,213 describes a process for the preparation of omeprazole by oxidation of pyrmetazole in the presence of meta-chloroperoxybenzoic acid. U.S. Patent Application No. 2003/0171591 discloses a method of producing benzimidazoles comprising oxidizing sulfide with an excess of oxidizing agent in the presence of a catalyst for asymmetric induction.

U.S. Pat. No. 6,229,021 describes a process for the preparation of omeprazole comprising oxidizing its corresponding thioether with peroxyacetic acid in a two-phase water and chlorinated organic solvent medium.

U.S. Pat. No. 6,268,502 describes a process for the preparation of omeprazole comprising oxidizing its corresponding thioether with 3-chloroperoxybenzoic acid in ethyl acetate. U.S. Pat. No. 6,603,009 discloses a process for the preparation of omeprazole comprising oxidizing its corresponding thioether with sodium percarbonate and molybdenum salt catalyst. U.S. Pat. No. 5,386,032 discloses a process for the preparation of omeprazole comprising oxidizing its corresponding thioether with m-chloroperoxybenzoic acid at specific pH.

U.S. Pat. No. 7,915,422 B2 discloses the enantioselective catalytic oxidation process for of a pro-chiral sulfide with an oxidizing agent in presence of chiral transition metal complex and a base in the absence of an organic solvent.

U.S. Patent Application No. 2010/0210848 A1 discloses the process for preparation of optically active sulfoxide compounds by asymmetrically oxidizing prochiral sulphide compounds in presence of chiral transition metal complex in water and in presence of a base.

International (PCT) publication WO 2003/089408 A2 discloses an enantioselective catalytic oxidation process for the preparation of on optically active enantiomer or an enantiomerically enriched form of substituted pyridinylmethylsulphinyl-benzimidazole with an oxidizing agent in an organic solvent in the presence of a base and a catalyst comprising titanium or vanadium complexed with a chiral mondenate ligand.

International (PCT) publication WO 99/47514 A2 discloses a method of producing benzimidazole compounds comprising oxidizing its corresponding thioether with perborate salt.

International (PCT) publication WO 03/089408 A2 describes an enantioselective catalytic oxidation of sulfide with an oxidizing agent, in an organic solvent, base and in the presence of titanium or vanadium complexed with a monodentate ligand.

International (PCT) publication WO 2008/018091A1 discloses the process for producing sulphoxide compounds in either as a single enantiomer or in an enantiomerically enriched form by asymmetrically oxidizing a prochiral sulfide with an oxidizing agent and a chiral transition metal complex without using an organic solvent and a base.

International (PCT) publication WO 2010/134099 A1 discloses a one-pot process for the preparation of omeprazole and related compounds.

Each and every reference in the prior art literature of which the inventors are aware discloses the process for the preparation of esomeprazole or other related chiral sulfoxide benzimidazole derivatives either by isolation of alkali metal salts of esomeprazole and converting to magnesium salt or by use of pyrmetazole as a prochiral sulfide as a starting material. No prior art literature which the inventors are aware discloses one pot process for the preparation of esomeprazole magnesium dihydrate starting from 2-(chloromethyl)-3,5-dimethyl-4-methoxy pyridine hydrochloride of Formula (V).

In view of the above, there is provided a one pot process for preparing benzimidazole derivatives and pharmaceutically acceptable salts thereof. In particular, the invention provides one pot process for enantioselective synthesis of single enantiomers of substituted sulphoxides 2-(2-pyridinylmethylsulphinyl)-1H-benzimidazoles or said compounds in an enantiomerically enriched form. More particularly, the invention provides one pot process for the preparation of esomeprazole magnesium dihydrate. Such improved processes and benzimidazole derivatives prepared thereby are now provided by the present invention substantially as herein described.

SUMMARY OF THE INVENTION

In one general aspect, the invention provides a one-pot process for preparing 2-[(pyridinyl)methyl]sulfinyl-benzimidazole derivative of Formula (II') or its pharmaceutically acceptable salt of Formula (I'), hydrate or solvate thereof, wherein M is alkali or alkaline earth metal salts; $R_1$ is selected from the group consisting of hydrogen or substituted or unsubstituted $C_1$-$C_4$alkoxy; $R_2$ and $R_4$ are independently selected from the group consisting of hydrogen, $C_1$-$C_4$alkyl or $C_1$-$C_4$alkoxy; $R_3$ is selected from the group consisting of substituted or unsubstituted $C_1$-$C_4$alkoxy, the process comprising:

(a) reacting 2-chloromethyl-substituted pyridine or salt thereof of Formula (V') with 2-mercapto-5-substituted benzimidazole of Formula (IV') in one or more of suitable organic solvent optionally in presence of base to obtain prochiral sulfide of Formula (III');

(b) asymmetrically oxidizing prochiral sulfide of Formula (III') in-situ with suitable oxidizing agent in one or more of suitable organic solvent in presence of chiral transition metal complex and optionally in the presence of a base to obtain optically active enantiomer or an enantiomerically enriched form of compound of Formula (II'), wherein $R_1$, $R_2$, $R_3$ and $R_4$ are the same as described above; and (c) optionally converting the optically active enantiomer or an enantiomerically enriched form of the compound of Formula (II') to pharmaceutically acceptable salts thereof of Formula (I'), hydrate or solvate thereof; and

(d) obtaining 2-[(pyridinyl)methyl]sulfinyl-benzimidazole derivative of Formula (II') or a pharmaceutically acceptable salt of Formula (I'), hydrate or a solvate thereof.

In another general aspect, the invention provides a one-pot process for preparing esomeprazole magnesium of Formula (I), or hydrate thereof, the process comprising:

(a) reacting 2-(chloromethyl)-3,5-dimethyl-4-methoxy pyridine or salt thereof of Formula (V) with 2-mercapto-5-methoxy benzimidazole of Formula (IV) in one or more of suitable organic solvent optionally in presence of base to obtain prochiral sulfide of Formula (III);

(b) asymmetrically oxidizing prochiral sulfide of Formula (III) in-situ with suitable oxidizing agent in one or more of suitable organic solvent in presence of chiral transition metal complex and optionally in presence of base to obtain esomeprazole compound of Formula (II);

(c) reacting esomeprazole compound of Formula (II) in-situ with a magnesium source to obtain esomeprazole magnesium of Formula (I); and
(d) converting esomeprazole magnesium to esomeprazole magnesium dihydrate.

In another general aspect, the invention provides a one-pot process for preparing esomeprazole magnesium of Formula (I) or a dihydrate thereof, the process comprising:

(a) reacting 2-(chloromethyl)-3,5-dimethyl-4-methoxy pyridine of Formula (V) or a salt thereof with 2-mercapto-5-methoxy benzimidazole of Formula (IV) in one or more organic solvents in the presence of a base to obtain prochiral sulfide of Formula (III);

(b) asymmetrically oxidizing prochiral sulfide of Formula (III) in-situ with a suitable oxidizing agent in one or more suitable organic solvents in the presence of a chiral transition metal complex, and optionally in the presence of a base to obtain esomeprazole compound of Formula (II) in a reaction mixture;

(c) treating the reaction mixture with a chlorinated solvent under acidic conditions;
(d) removing the chlorinated solvent to obtain a residue;
(e) reacting the residue with a magnesium source to obtain esomeprazole magnesium of Formula (I) in a suitable first solvent;
(f) removing the suitable first solvent to obtain a residue; and
(g) treating the residue with a second solvent to obtain esomeprazole magnesium dihydrate.

In another general aspect, the invention provides a pharmaceutical composition comprising a therapeutically effective amount of esomeprazole magnesium dihydrate having percentage crystallinity in the range of 45% to 65% together with one or more pharmaceutically acceptable carriers, excipients or diluents.

DETAILED DESCRIPTION OF THE INVENTION

All ranges recited herein include the endpoints, including those that recite a range "between" two values. Terms such as "about", "general", "substantially" and the like are to be construed as modifying a term or value such that it is not an absolute. Such terms will be defined by the circumstances and the terms that they modify as those terms are understood by those skill in the art. This includes, at very least, the degree of expected experimental error, technique error and instrument error for a given technique used to measure a value.

As used herein, the term "obtaining" may include isolation of desired compound by way of filtration, filtration under vacuum, centrifugation, and decantation. The product obtained may be further or additionally dried to achieve the desired moisture values. For example, the product may be dried in a tray drier, dried under vacuum and/or in a Fluid Bed Drier.

Optionally, the solution, prior to any solids formation, may be filtered to remove any undissolved solids, solid impurities and the like prior to removal of the solvent. Any filtration system and filtration techniques known in the art can be used.

The term "ambient temperature" used herein means, slurrying the reaction mixture either heterogeneous or homogeneous at a temperature from about 10° C. to about 35° C. of solvent.

"Suitable solvent" means a single or a combination of two or more solvents.

In one general aspect, the invention provides a one-pot process for preparing 2-[(pyridinyl)methyl]sulfinyl-benzimidazole derivative of Formula (II') or a pharmaceutically acceptable salt of Formula (I'), hydrate or a solvate thereof, wherein M is alkali or alkaline earth metal salts; $R_1$ is selected from the group consisting of hydrogen or substituted or unsubstituted $C_1$-$C_4$alkoxy; $R_2$ and $R_4$ are independently selected from the group consisting of hydrogen, $C_1$-$C_4$alkyl or $C_1$-$C_4$alkoxy; $R_3$ is selected from the group consisting of substituted or unsubstituted $C_1$-$C_4$alkoxy, the process comprising:

(a) reacting 2-chloromethyl-substituted pyridine or salt thereof of Formula (V') with 2-mercapto-5-substituted benzimidazole of Formula (IV') in one or more of suitable organic solvent optionally in presence of base to obtain prochiral sulfide of Formula (III');

(b) asymmetrically oxidizing prochiral sulfide of Formula (III') in-situ with suitable oxidizing agent in one or more of suitable organic solvent in presence of chiral transition metal complex and optionally in presence of base to obtain optically active enantiomer or an enantiomerically enriched form of compound of Formula (II');

wherein $R_1$, $R_2$, $R_3$ and $R_4$ is same as described above, (c) optionally, converting the optically active enantiomer or an enantiomerically enriched form of the compound of Formula (II') to a pharmaceutically acceptable salt thereof of Formula (I'), hydrate or solvate thereof; and (d) obtaining 2-[(pyridinyl)methyl]sulfinyl-benzimidazole derivative of Formula (II') or a pharmaceutically acceptable salt of Formula (I'), hydrate or a solvate thereof.

In general, the process according to the present invention may comprise conversion of a enantiomerically pure 2-[(pyridinyl)methyl]sulfinyl-substituted benzimidazole compounds of Formula (II') to a suitable pharmaceutically acceptable salt of Formula (I'), hydrate or solvate thereof. In particular a pharmaceutically acceptable salt may be selected from alkali or alkaline earth metals, for example Mg, Ca, Na, K or Li salts. More particularly, Mg or Na salts.

In the case, where $R_1$ represents substituted alkoxy substantially as hereinbefore described, suitable substituents include one or more halo substituents, such as one or more fluoro substituents.

In the case, where $R_3$ represents substituted alkoxy substantially as hereinbefore described, suitable substituents include one or more halo substituents, such as one or more fluoro substituents, or one or more alkoxy substituents, such as $C_1$-$C_3$ alkoxy, especially methoxy.

In general, $R_1$ comprises one or more of hydrogen atom, methoxy group or difluoromethoxy group; represents methyl group or methoxy group; $R_2$ comprises one or more of methyl group or methoxy group; $R_3$ comprises one or more of 3-methoxypropoxy group, methoxy group or 2,2,2-trifluoroethoxy group; and $R_4$ comprises one or more of hydrogen atom or methyl group.

In particular, the preferred compound prepared according to the process of the present invention is (R)-lansoprazole or (S)-lansoprazole, wherein in Formula (I'), $R_4$ represents methyl, $R_3$ represents trifluoroethoxy, $R_2$ represents hydrogen and $R_1$ represents hydrogen.

In particular, the preferred compound prepared according to the process of the present invention is (S)-omeprazole or (R)-omeprazole, wherein in Formula (I') $R_4$ represents methyl, $R_3$ represents methoxy, R2 represents methyl and $R_1$ represents methoxy.

In particular, the preferred compound prepared according to the process of the present invention is (S)-pantoprazole or (R)-pantoprazole, wherein in Formula (I') $R_4$ represents methoxy, $R_3$ represents methoxy, $R_2$ represents hydrogen and $R_1$ represents difluoromethoxy.

In particular, the preferred compound prepared according to the process of the present invention is (S)-rabeprazole or (R)-rabeprazole, wherein in Formula (I) $R_4$ represents methyl, $R_3$ represents —$OCH_2CH_2CH_2OMe$, $R_2$ represents hydrogen and $R_1$ represents hydrogen.

In general, the condensation of compound of general Formula (V') and (IV') may be performed in a suitable solvent comprising one or more of alcohols like methanol, ethanol, isopropanol, butanol, tert-butanol, esters like ethyl acetate, isopropyl acetate, tert-butyl acetate, n-butyl acetate and the like, ketones like acetone, methyl ethyl ketone, methyl isobutyl ketone, and the like. In particular, methanol may be used. The condensation may be carried out in the presence of a base comprising one or more of alkali metal or alkaline earth metal hydroxide, alkoxide, carbonates, bicarbonates, hydrides or ammonia, and the like.

In general, the suitable base comprises one or more of sodium hydroxide, potassium hydroxide, lithium hydroxide, sodium methoxide, sodium ethoxide, potassium tert-butoxide, sodium carbonate, potassium carbonate, sodium bicarbonate, potassium bicarbonate, sodium hydride or ammonia. In particular, sodium hydroxide may be used.

The embodiments of the process includes condensation of the compound of general Formula (V') and (IV') in methanol solvent at 25° C. in the presence of a base like sodium hydroxide. The condensed product may be preceded directly for oxidation step without isolation.

In general, the embodiments of the process include the chiral oxidation of the compound of Formula (II'), and may be carried out in the presence of a base. Alternatively, the oxidation can be carried out in the absence of a base, if the preparation of the chiral titanium complex is performed in a specific way with respect to the order of addition, preparation temperature and/or preparation time.

In general, the process includes the preparation of the chiral titanium complex during an elevated temperature and/or during a prolonged preparation time. The titanium complex suitable for catalyzing the process of the invention may be prepared from a chiral ligand and a titanium(IV) compound, optionally in the presence of water. The titanium(IV) compound comprises titanium(IV)alkoxide like titanium(IV) isopropoxide or titanium(IV)propoxide.

The titanium complex may also be prepared by reacting titanium tetrachloride with a chiral ligand in the presence of a base. The chiral ligand used in the preparation of the titanium complex may be particularly a chiral alcohol such as a chiral diol. The diol may be a branched or unbranched alkyl diol, or an aromatic diol. Particular chiral diols are esters or tartaric acid, especially (+)-diethyl L-tartrate or (−)-diethyl D-tartrate are preferred. In general, an oxidizing agent suitable for oxidation may be selected from tert-butylhydroperoxide or cumene hydroperoxide and the like.

The oxidation may be performed in one or more suitable organic solvents. Suitable organic solvents include one or more of alcohols like methanol, ethanol, isopropanol, n-propanol, n-butanol, tert-butanol, isobutanol and the like, hydrocarbons like octane, isooctane, toluene, xylene, ethylbenzene and the like, ethers like diethyl ether, diisopropyl ether, methyl tert-butyl ether, tetrahydrofuran and the like, esters like ethyl acetate, methyl acetate, isopropyl acetate, butyl acetate and the like, dimethylformamide, dimethyl sulfoxide, methyl ethyl ketone, methyl isobutyl ketone, diethyl carbonate, tetrahydrofuran, methylene chloride, and the like or mixtures thereof. In particular, toluene may be used.

The oxidation may be particularly carried out in an organic solvent at ambient temperature. For example, it may be carried out from about 10-25° C. A suitable temperature range may be limited only depending on the decomposition of the compounds, and that the reaction time may be drastically shorter at room temperature than at −20° C.

In general, the base comprises one or more of an inorganic base selected from sodium hydroxide, potassium hydroxide, sodium methoxide, potassium methoxide, sodium bicarbonate, potassium bicarbonate, sodium carbonate, potassium carbonate, potassium tert-butoxide and the like or an organic bases comprises one or more of triethylamine, diethylamine, tert-butylamine, N,N-diisopropylamine, N,N-diisopropylethylamine, pyridine, piperidine, DBU, DABCO and the like. In particular, the suitable bases are amines, particularly triethylamine or N,N-diisopropylethylamine.

In another general aspect, the invention provides a one-pot process for preparing esomeprazole magnesium of Formula (I), or hydrate thereof, the process comprising:
(a) reacting 2-(chloromethyl)-3,5-dimethyl-4-methoxy pyridine or salt thereof of Formula (V) with 2-mercapto-5-methoxy benzimidazole of Formula (IV) in one or more of suitable organic solvent optionally in presence of base to obtain prochiral sulfide of Formula (III);

(b) asymmetrically oxidizing prochiral sulfide of Formula (III) in-situ with suitable oxidizing agent in one or more of suitable organic solvent in presence of chiral transition metal complex and optionally in presence of base to obtain esomeprazole compound of Formula (II);

(c) reacting esomeprazole compound of Formula (II) in-situ with a magnesium source to obtain esomeprazole magnesium of Formula (I); and
(d) converting the esomeprazole magnesium to esomeprazole magnesium dihydrate.

In general, the condensation of compound of general Formula (V) and (IV) may be performed in one or more of suitable solvent comprises alcohols like methanol, ethanol, isopropanol, butanol, tert-butanol, esters like ethyl acetate, isopropyl acetate, tert-butyl acetate, n-butyl acetate and the like, ketones like acetone, methyl ethyl ketone, methyl isobutyl ketone and the like. In particular, methanol may be used. The condensation can be carried out in presence of base comprises one or more of alkali metal or alkaline earth metal hydroxide, alkoxide, carbonates, bicarbonates, hydrides or ammonia and the like.

In general, the suitable base comprises one or more of sodium hydroxide, potassium hydroxide, lithium hydroxide, sodium methoxide, sodium ethoxide, potassium tert-butoxide, sodium carbonate, potassium carbonate, sodium bicarbonate, potassium bicarbonate, sodium hydride or ammonia. In particular, sodium hydroxide may be used.

The embodiments of the process include condensation of compound of general Formula (V) and (IV) in methanol solvent at 25° C. in presence of base like sodium hydroxide. The condensed product may be preceded directly for oxidation step without isolation.

In general, the embodiments of the process include the chiral oxidation of the compound of Formula (II) which may be carried out in the presence of a base. Alternatively, the oxidation can be carried out in the absence of a base if the preparation of the chiral titanium complex is performed in a specific way with respect to the order of addition, preparation temperature and/or preparation time.

In general, the process includes the preparation of the chiral titanium complex during an elevated temperature and/or during a prolonged preparation time. The titanium complex suitable for catalyzing the process of the invention may be prepared from a chiral ligand and a titanium(IV) compound, optionally in the presence of water. The titanium(IV) compound comprises titanium(IV)alkoxide like titanium(IV) isopropoxide or titanium(IV)propoxide.

The titanium complex may also be prepared by reacting titanium tetrachloride with a chiral ligand in the presence of a base. The chiral ligand used in the preparation of the titanium complex may be particularly a chiral alcohol such as a chiral diol. The diol may be a branched or unbranched alkyl diol, or an aromatic diol. Particular chiral diols are esters or tartaric acid, especially (+)-diethyl L-tartrate or (−)-diethyl D-tartrate are preferred.

In general, an oxidizing agent suitable for oxidation may be selected from tert-butylhydroperoxide or cumene hydroperoxide and the like.

The oxidation may be performed in one or more of suitable organic solvent. Suitable organic solvents comprises one or more of alcohols like methanol, ethanol, isopropanol, n-propanol, n-butanol, tert-butanol, isobutanol and the like, hydrocarbons like octane, isooctane, toluene, xylene, ethylbenzene and the like, ethers like diethyl ether, diisopropyl ether, methyl tert-butyl ether, tetrahydrofuran and the like, esters like ethyl acetate, methyl acetate, isopropyl acetate, butyl acetate and the like, dimethylformamide, dimethyl sulfoxide, methyl ethyl ketone, methyl isobutyl ketone, diethyl carbonate, tetrahydrofuran, methylene chloride and the like or mixture thereof. In particular, toluene may be used.

The oxidation may be particularly carried out in an organic solvent at ambient temperature. For example, it may be carried out from about 10-25° C. A suitable temperature range may be limited only depending on the decomposition of the compounds, and that the reaction time may be drastically shorter at room temperature than at −20° C.

In general, the base comprises one or more of an inorganic base like sodium hydroxide, potassium hydroxide, sodium methoxide, potassium methoxide, sodium bicarbonate, potassium bicarbonate, sodium carbonate, potassium carbonate, potassium tert-butoxide and the like or an organic bases comprises one or more of triethylamine, diethylamine, tert-butylamine, N,N-diisopropylamine, N,N-diisopropylethylamine, pyridine, piperidine, DBU, DABCO and the like. In particular, the suitable bases are amines, particularly triethylamine or N,N-diisopropylethylamine.

In another general aspect, benzimidazole derivatives may be prepared by the reaction scheme-1 as shown below, which is also within the scope of the present invention.

Scheme-1

In another general aspect, esomeprazole magnesium may be prepared by the reaction scheme-2 as shown below, which is also the scope of the present invention.

In another general aspect, the invention provides a one-pot process for preparing esomeprazole magnesium of Formula (I) or dihydrate thereof.

Scheme-2 the process comprising:
(a) reacting 2-(chloromethyl)-3,5-dimethyl-4-methoxy pyridine or salt thereof of Formula (V) with 2-mercapto-5-methoxy benzimidazole of Formula (IV) in one or more of organic solvent in presence of base to obtain prochiral sulfide of Formula (III);

(b) asymmetrically oxidizing prochiral sulfide of Formula (III) in-situ with suitable oxidizing agent in one or more of suitable organic solvent in presence of chiral transition metal complex and optionally in presence of base to obtain esomeprazole compound of Formula (II) in reaction mixture;

(c) treating the reaction mixture with chlorinated solvent under acidic conditions;
(d) removal of chlorinated solvent to obtain residue;
(e) reacting residue with a magnesium source to obtain esomeprazole magnesium of Formula (I) in one or more of first solvent;
(f) removal of suitable solvent to obtain residue and
(g) treating the residue with second solvent to obtain esomeprazole magnesium dihydrate.

In general, the process embodiments includes condensation of 2-(chloromethyl)-3,5-dimethyl-4-methoxy pyridine of its hydrochloride of Formula (V) with 2-mercapto-5-methoxy benzimidazole of Formula (IV) in suitable solvents like methanol in presence of suitable base like sodium hydroxide to obtain prochiral sulfide (III). The reaction may be performed at 25° C. The product may be preceded without isolation of prochiral sulfide (III).

In general, the oxidation of prochiral sulfoxide may be performed using cumene hydroperoxide in presence of transition metal complex like titanium isopropoxide and D-(−)-diethyl tartrate and a base like N,N-diisopropylethylamine. The oxidation may be performed in suitable solvent like toluene followed by addition of small quantity of water.

The process parameters further includes, treating the reaction mixture containing the oxidized product with chlorinated solvent comprises one or more of methylene dichloride, chlorobenzene, chloroform, ethylene dichloride and the like. In particular, methylene dichloride may be used. The reaction mixture may be treated with methylene dichloride under acidic conditions like 10% glacial acetic acid to adjust the pH from about 6 to 8.

Further, the process embodiments provides distillation of reaction mixture under vacuum to removal methylene dichloride to obtain residue which is treated with magnesium source like magnesium acetate, magnesium sulfate, magnesium methoxide and the like. In particular magnesium methoxide. The reaction may be particularly performed in a suitable first solvent comprises one or more of methanol, ethanol, isopropanol, butanol and the like. In particular, methanol may be used.

The first solvent may be removed by distillation to obtain residue which may treated with suitable second solvent like ketones comprises one or more of acetone, methyl isobutyl ketone, methyl ethyl ketone and the like. In particular, acetone may be used. The product thus obtained may be dried under usual conditions till residual solvents are under ICH limits to obtain esomeprazole magnesium dihydrate.

Figure 1:
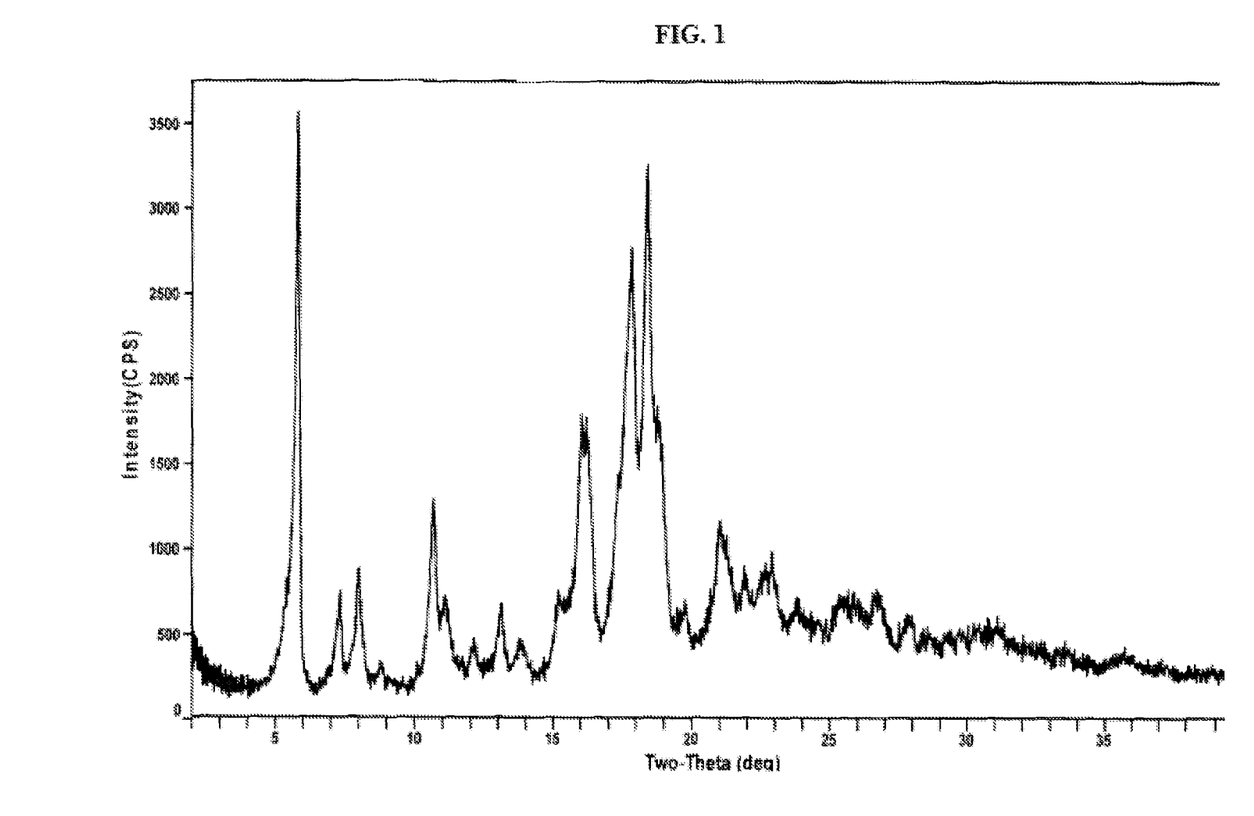
FIG. 1: X-ray powder diffraction of esomeprazole magnesium dihydrate prepared by the process of the present invention.
Figure 2:
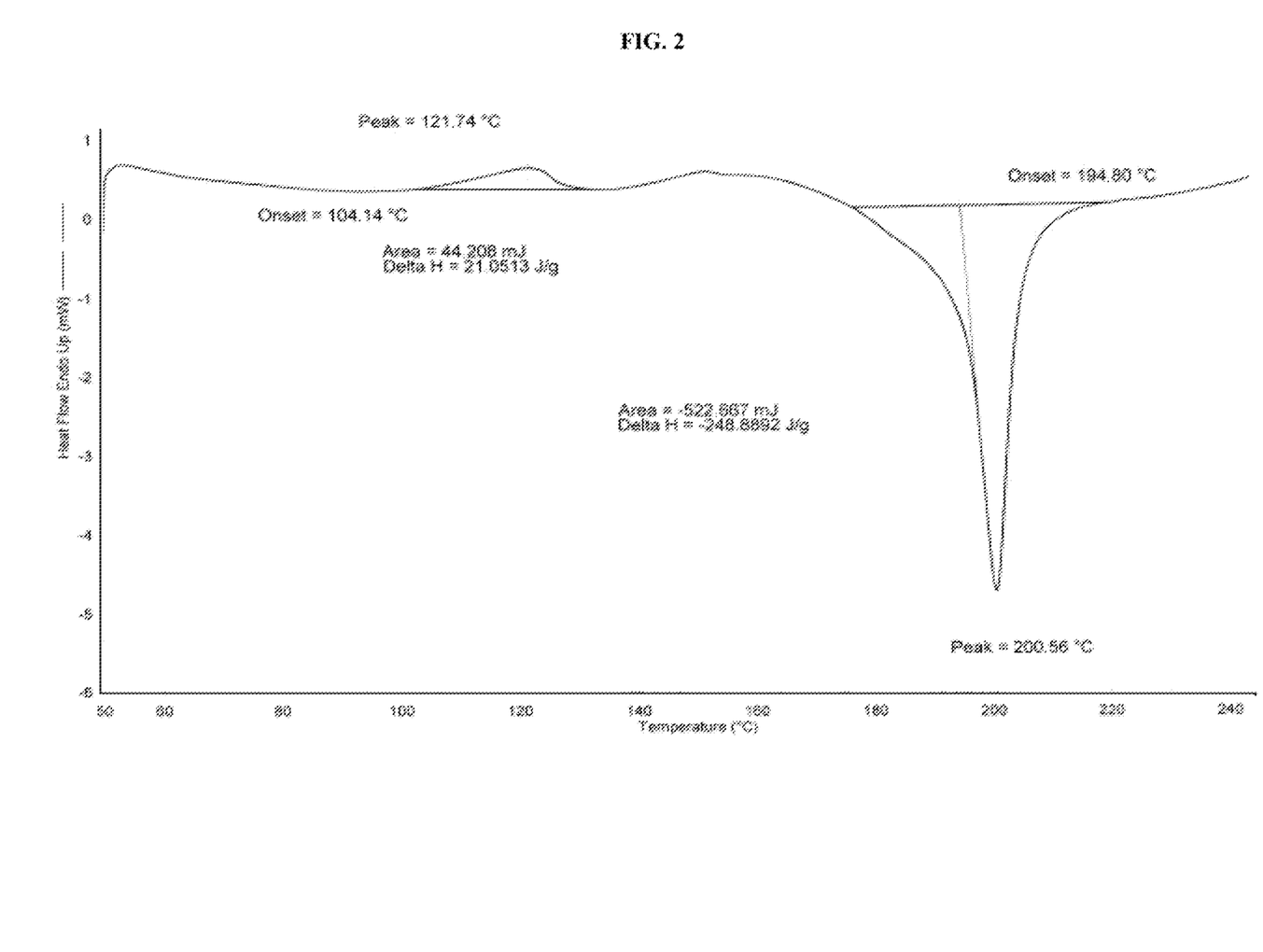
FIG. 2: Differential scanning calorimetry of esomeprazole magnesium dihydrate prepared by the process of present invention.

The product esomeprazole magnesium dihydrate may be characterized by X-ray powder diffraction pattern substantially as depicted in FIG. 1 and differential scanning calorimetry substantially as depicted in FIG. 2.

In one general aspect, the present invention provides esomeprazole magnesium dihydrate prepared by the process of present invention having percentage crystallinity in the range of 45% to 65%.

Powder X-ray diffraction of esomeprazole magnesium dihydrate may be obtained under following conditions:
(i) characterization by Powder X-ray diffraction
The X-ray powder diffraction spectrum was measured under the following experimental conditions:
Instrument: X-Ray Diffractometer, D/Max-2200/PC Make: Rigaku, Japan.
X-Ray: Cu/40 kv/40 mA
Diverging: 10
Scattering Slit: 10
Receiving Slit: 0.15 mm
Monochromator RS: 0.8 mm
Counter: Scintillation Counter
Scan Mode: Continuous
Scan Speed: 3.0000/Min
Sampling Width: 0.020
Scan Axes: Two Theta/Theta
Scan Range: 2.0000 to 40.0000
Theta Offset: 0.0000

In another general aspect, there is provided a pharmaceutical composition comprising a therapeutically effective amount of esomeprazole magnesium dihydrate having percentage crystallinity in the range of 45% to 65% together with one or more pharmaceutically acceptable carriers, excipients or diluents.

As used herein, the term "pharmaceutical compositions" or "pharmaceutical Formulations" includes tablets, pills, powders, liquids, suspensions, emulsions, granules, capsules, suppositories, or injection preparations.

Pharmaceutical compositions containing the esomeprazole magnesium dihydrate of the invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

The present invention is further illustrated by the following examples which are provided merely to be exemplary of the invention and do not limit the scope of the invention. Certain modification and equivalents will be apparent to those skilled in the art and are intended to be included within the scope of the present invention.

EXAMPLES

Example-1

Preparation of Esomeprazole Magnesium Dihydrate
(One-Pot Process)

2-(chloromethyl)-3,5-dimethyl-4-methoxy pyridine hydrochloride (70 g) and 2-mercapto-5-methoxybenzimidazole (57.4 g) were taken in methanol (245 mL) at 25° C. and sodium hydroxide (31.5 g) solution in water was added. The reaction mixture was stirred for 45 min and quenched in water (490 mL). The reaction mixture was acidified with 10% glacial acetic acid (75 mL) and extracted with toluene (350 mL). The toluene extract was washed with water and partially distilled for azeotropic removal of water. The reaction mixture was cooled to 25° C. and water (0.68 mL), D-(−)-Diethyl tartrate (38.2 g), Titanium isopropoxide (28.5 g) were added. The reaction mixture was heated to 50° C. for 1 hour and cooled to 0° C. Diisopropylethylamine (12 g) and cumene hydroperoxide (80%) (60 g) were added and stirred for 20 min at 15° C. The reaction mixture was stirred for 8 hours at 15° C. Sodium thiosulfate (14.4 g) aqueous solution and aqueous sodium hydroxide (60 g) solution were added to the reaction mixture. The separated aqueous layer was treated with methylene dichloride (500 mL) and acidified with glacial acetic acid to adjust the pH of 6.5. The separated organic layer was distilled under vacuum to obtain residue. Methanol (250 mL) was added to the residue and magnesium methoxide solution (3.3 g) in methanol:methylene dichloride (100:8 mL) was added at 25° C. The reaction mixture was stirred for 9 hours and catalytic amount of water (1.0 mL) was added. The reaction mixture was filtered and washed with methanol (70 mL). The filtrate was treated with charcoal and distilled under vacuum to obtain residue. Acetone (50 mL) was added to the residue and stirred for 2 hours at 25° C. The slurry was filtered and washed with acetone/methanol (90:10 mL) and dried to obtain wet-cake (95 g) of esomeprazole magnesium. The wet-cake was dissolved in methanol (350 mL) and charcoalized. The reaction mixture was filtered and methanol was partially distilled from filtrate to obtain residue with 3 times of methanol. Acetone (800 mL) was added to the residue at 25° C. and stirred for 2 hours. The reaction mixture was filtered and wet-cake was washed with acetone/methanol (90:10 mL). The product was dried in tray drier followed by vacuum drying till residual solvents are within the ICH limits to obtain 77 g esomeprazole magnesium dihydrate. Water content 6.15% (by KF), X-ray powder diffraction (FIG. 1) and Differential scanning calorimetry (FIG. 2).

Example-2

Preparation of Esomeprazole Magnesium Dihydrate
(One-Pot Process)

2-(chloromethyl)-3,5-dimethyl-4-methoxy pyridine hydrochloride (300 g) and 2-mercapto-5-methoxybenzimidazole (245.9 g) were taken in methanol (1050 mL) at 25° C. and sodium hydroxide (135 g) solution in water was added. The reaction mixture was stirred for 45 min and quenched in water (2100 mL). The reaction mixture was acidified with 10% glacial acetic acid (322 mL) and extracted with toluene (1500 mL). The toluene extract was washed with water and partially distilled for azeotropic removal of water. The reaction mixture was cooled to 25° C. and water (2.9 mL), D-(−)-Diethyl tartrate (163.7 g), Titanium isopropoxide (122.9 g) were added. The reaction mixture was heated to 50° C. for 1 hour and cooled to 0° C. Diisopropylethylamine (52.4 g) and cumene hydroperoxide (80%) (257 g) were added and stirred for 20 min at 15° C. The reaction mixture was stirred for 8 hours at 15° C. Sodium thiosulfate (61.7 g) aqueous solution and aqueous sodium hydroxide (257.1 g) solution were added to the reaction mixture. The separated aqueous layer was treated with methylene dichloride (2150 mL) and acidified with glacial acetic acid to adjust the pH of 6.5. The separated organic layer was distilled under vacuum to obtain residue. Methanol (1050 mL) was added to the residue and magnesium methoxide solution (14.14 g) in methanol:methylene dichloride (428:35 mL) was added at 25° C. The reaction mixture was stirred for 9 hours and catalytic amount water (4.3 mL) was added. The reaction mixture was filtered and washed with methanol (300 mL). The filtrate was treated with charcoal and distilled under vacuum to obtain residue. Acetone (50 mL) was added to the residue and stirred for 2 hours at 25° C. The slurry was filtered and washed with acetone/methanol (385:43 mL) and dried to obtain wet-cake (416 g) of esomeprazole magnesium. The wet-cake was dissolved in methanol (1500 mL) and charcoalized. The reaction mixture was filtered and methanol was partially distilled from filtrate to obtain residue with 3 times of methanol. Acetone (3428 mL) was added to the above residue at 25° C. and stirred for 2 hours. The reaction mixture was filtered and wet-cake was washed with acetone/methanol (385:43 mL). The product was dried in fluid bed dryer for 3 hours at 25° C. to obtain 305 g esomeprazole magnesium dihydrate with residual solvents within ICH limits. Water content 6.09% (by KF), X-ray powder diffraction (FIG. 1) and Differential scanning calorimetry (FIG. 2).

The process parameters may be repeated in similar manner of example-1 by using 2-(chloromethyl)-3-methyl-4-(2,2,2-trifluoroethoxy)pyridine hydrochloride and 2-mercapto-enzimidazole as starting materials to obtain dexlansoprazole. The proviso that appropriate Diethyl tartrate may be selected for resolution to obtain specific stereoselectivity and converting to its pharmaceutically acceptable salts if required.

While the present invention has been described in terms of its specific embodiments, certain modifications and equivalents will be apparent to those skilled in the art and are intended to be included within the scope of the present invention.

We claim:

1. A one-pot process for preparing 2-[(pyridinyl)methyl]sulfinyl-benzimidazole derivative of Formula (II') or a pharmaceutically acceptable salt of Formula (I'), hydrate or a solvate thereof, wherein M is alkali or alkaline earth metal salts;

$R_1$ is selected from the group consisting of hydrogen or substituted or unsubstituted $C_1$-$C_4$alkoxy;

$R_2$ and $R_4$ are independently selected from the group consisting of hydrogen, $C_1$-$C_4$alkyl or $C_1$-$C_4$alkoxy;

$R_3$ is selected from the group consisting of substituted or unsubstituted $C_1$-$C_4$alkoxy, the process comprising:

(a) reacting 2-chloromethyl-substituted pyridine of Formula (V') or a salt thereof with 2-mercapto-5-substituted benzimidazole of Formula (IV') in one or more suitable organic solvents, optionally in the presence of a base to obtain prochiral sulfide of Formula (III');

(b) asymmetrically oxidizing prochiral sulfide of Formula (III') in-situ with an oxidizing agent in one or more organic solvents in the presence of a chiral transition metal complex, and optionally in the presence of a base to obtain optically active enantiomer or an enantiomerically enriched form of a compound of Formula (II');

wherein $R_1$, $R_2$, $R_3$ and $R_4$ are the same as described above;

(c) optionally, converting the optically active enantiomer or an enantiomerically enriched form of the compound of Formula (II') to a pharmaceutically acceptable salt thereof of Formula (I'), hydrate or solvate thereof; and (d) obtaining 2-[(pyridinyl)methyl]sulfinyl-benzimidazole derivative of Formula (II') or a pharmaceutically acceptable salt of Formula (I'), hydrate or a solvate thereof.

2. The process according to claim 1, wherein $R_4$ represents methyl, $R_3$ represents trifluoroethoxy, $R_2$ represents hydrogen and $R_1$ represents hydrogen.

3. The process according to claim 1, wherein $R_4$ represents methyl, $R_3$ represents methoxy, R2 represents methyl and $R_1$ represents methoxy.

4. The process according to claim 1, wherein $R_4$ represents methoxy, $R_3$ represents methoxy, $R_2$ represents hydrogen and $R_1$ represents difluoromethoxy.

5. The process according to claim 1, wherein $R_4$ represents methyl, $R_3$ represents —$OCH_2CH_2CH_2OMe$, $R_2$ represents hydrogen and $R_1$ represents hydrogen.

6. The process according to claim 1, wherein in step (a) of claim 1 the organic solvent comprises one or more of alcohols like methanol, ethanol, isopropanol, butanol, tert-butanol; esters selected from ethyl acetate, isopropyl acetate, tert-butyl acetate, and n-butyl acetate; and ketones selected acetone, methyl ethyl ketone, and methyl isobutyl ketone.

7. The process according to claim 1, wherein the base comprises one or more of sodium hydroxide, potassium hydroxide, lithium hydroxide, sodium methoxide, sodium ethoxide, potassium tert-butoxide, sodium carbonate, potassium carbonate, sodium bicarbonate, potassium bicarbonate, sodium hydride or ammonia.

8. The process according to claim 1, wherein in step (b) of claim 1 the organic solvent comprises one or more of alcohols like methanol, ethanol, isopropanol, n-propanol, n-butanol, tert-butanol, isobutanol and the like, hydrocarbons like octane, isooctane, toluene, xylene, ethylbenzene; ethers selected diethyl ether, diisopropyl ether, methyl tert -butyl ether, tetrahydrofuran; esters selected from ethyl acetate, methyl acetate, isopropyl acetate, butyl acetate; and dimethylformamide, dimethyl sulfoxide, methyl ethyl ketone, methyl isobutyl ketone, diethyl carbonate, tetrahydrofuran, methylene chloride, or mixtures thereof.

9. The process according to claim 1, wherein in step (b) of claim 1 the oxidizing agent comprises one or both of tert-butylhydroperoxide and cumene hydroperoxide.

10. The process according to claim 1, wherein in step (b) of claim 1 the base comprises an inorganic base selected from sodium hydroxide, potassium hydroxide, sodium methoxide, potassium methoxide, sodium bicarbonate, potassium bicarbonate, sodium carbonate, potassium carbonate, and potassium tert-butoxide; an organic base selected from one or more of triethylamine, diethylamine, tert-butylamine, N,N-diisopropylamine, N,N-diisopropylethylamine, pyridine, piperidine, DBU, and DABCO.

11. The process according to claim 1, wherein in step (b) of claim 1 the chiral transition metal complex is prepared from a chiral ligand and a titanium (IV) compound, comprising titanium(IV)isopropoxide or titanium(IV)propoxide, optionally in the presence of water.

12. The process according to claim 1, wherein pharmaceutically acceptable salts of Formula (I') comprises alkali or alkaline earth metals like Mg, Ca, Na, K or Li salts.

13. One pot process for preparing esomeprazole magnesium of Formula (I), or a hydrate thereof, the process comprising:
(a) reacting 2-(chloromethyl)-3,5-dimethyl-4-methoxy pyridine of Formula (V) or a salt thereof with 2-mercapto-5-methoxy benzimidazole of Formula (IV) in one or more organic solvents, optionally in the presence of a base to obtain prochiral sulfide of Formula (III), Prochiral sulfide (b) asymmetrically oxidizing prochiral sulfide of Formula (III) in-situ with a oxidizing agent in one or more organic solvents in the presence of a chiral transition metal complex, and optionally in the presence of a base to obtain esomeprazole compound of Formula (II), (c) reacting esomeprazole compound of Formula (II) in-situ with a magnesium source to obtain the esomeprazole magnesium of Formula (I); and
(d) converting the esomeprazole magnesium to esomeprazole magnesium dihydrate.

14. The process according to claim 13, wherein in step (a) of claim 15 the organic solvent comprises one or more of alcohols selected from methanol, ethanol, isopropanol, butanol, tert-butanol; esters selected from ethyl acetate, isopropyl acetate, tert-butyl acetate, n-butyl acetate; and ketones selected from acetone, methyl ethyl ketone, and methyl isobutyl ketone.

15. The process according to claim 13, wherein in step (a) of claim 15 the base comprises one or more of sodium hydroxide, potassium hydroxide, lithium hydroxide, sodium methoxide, sodium ethoxide, potassium tert-butoxide, sodium carbonate, potassium carbonate, sodium bicarbonate, potassium bicarbonate, sodium hydride or ammonia.

16. The process according to claim 13, wherein in step (b) of claim 15 wherein the organic solvent comprises one or more of alcohols selected from methanol, ethanol, isopropanol, n-propanol, n-butanol, tert-butanol, and isobutanol; hydrocarbons selected from octane, isooctane, toluene, xylene, and ethylbenzene; ethers selected from diethyl ether, diisopropyl ether, methyl tert-butyl ether, tetrahydrofuran; esters selected from ethyl acetate, methyl acetate, isopropyl acetate, butyl acetate; dimethylformamide, dimethyl sulfoxide, methyl ethyl ketone, methyl isobutyl ketone, diethyl carbonate, tetrahydrofuran, methylene chloride, or mixtures thereof.

17. The process according to claim 13, wherein the oxidizing agent comprises one or both of tert-butylhydroperoxide or cumene hydroperoxide.

18. The process according to claim 13, wherein in step (b) of claim 15 the base comprises an inorganic base selected from one or more sodium hydroxide, potassium hydroxide, sodium methoxide, potassium methoxide, sodium bicarbonate, potassium bicarbonate, sodium carbonate, potassium carbonate, potassium tert-butoxide; an organic base selected from one or more of triethylamine, diethylamine, tert-butylamine, N,N-diisopropylamine, N,N-diisopropylethylamine, pyridine, piperidine, DBU, and DABCO.

19. The process according to claim 13, wherein in step (b) of claim 15 the chiral titanium metal complex is prepared from a chiral ligand and a titanium(IV) compound comprising titanium(IV)isopropoxide or titanium(IV)propoxide, optionally in the presence of water.

20. A one-pot process for preparing esomeprazole magnesium of Formula (I) or a dihydrate thereof, the process comprising:
(a) reacting 2-(chloromethyl)-3,5-dimethyl-4-methoxy pyridine of Formula (V) or a salt thereof with 2-mercapto-5-methoxy benzimidazole of Formula (IV) in one or more organic solvents in the presence of a base to obtain prochiral sulfide of Formula (III);

(b) asymmetrically oxidizing prochiral sulfide of Formula (III) in-situ with an oxidizing agent in one or more organic solvents in the presence of a chiral transition metal complex, and optionally in the presence of a base to obtain esomeprazole compound of Formula (II) in a reaction mixture;

(c) treating the reaction mixture with a chlorinated solvent under acidic conditions;

(d) removing the chlorinated solvent to obtain a residue;

(e) reacting the residue with a magnesium source to obtain esomeprazole magnesium of Formula (I) in a suitable first solvent;

(f) removing the suitable first solvent to obtain a residue; and (g) treating the residue with a suitable second solvent to obtain esomeprazole magnesium dihydrate.

21. The process according to claim 20 wherein in step (a) of claim 20 the organic solvent is methanol.

22. The process according to claim 20 wherein in step (a) of claim 20 the base is sodium hydroxide.

23. The process according to claim 20 wherein in step (b) of claim 20 the organic solvent is toluene.

24. The process according to claim 20, wherein in step (b) of claim 20 the oxidizing agent comprises one or both of tert-butylhydroperoxide and cumene hydroperoxide.

25. The process according to claim 20 wherein in step (b) of claim 20 the base is N,N-diisopropylamine.

26. The process according to claim 20 wherein the chlorinated solvent comprises one or more of methylene dichloride, chlorobenzene, chloroform, and ethylene dichloride.

27. The process according to claim 20 wherein the first organic solvent comprises one or more of methanol, ethanol, isopropanol, and butanol.

28. The process according to claim 20 wherein the second organic solvent comprises one or more of acetone, methyl isobutyl ketone, and methyl ethyl ketone.

* * * * *